(12) United States Patent
Guedat et al.

(10) Patent No.: US 7,462,615 B2
(45) Date of Patent: Dec. 9, 2008

(54) INHIBITORS OF CYSTEINE PROTEASES, THE PHARMACEUTICAL COMPOSITIONS THEREOF AND THEIR THERAPEUTIC APPLICATIONS

(75) Inventors: Philippe Guedat, Montenois (FR); Guillaume Boissy, Vincennes (FR); Catherine Borg-Capra, Suresnes (FR); Frédéric Colland, Puiseux en France (FR); Laurent Daviet, Antony (FR); Etienne Formstecher, Paris (FR); Xavier Jacq, Paris (FR); Jean-Christophe Rain, Ermont (FR); Rémi Delansorne, Paris (FR); Ilaria Peretto, Ceriano Laghetto (IT); Stefano Vignando, Milan (IT)

(73) Assignee: Hybrigenics SA, Paris (FR)

( * ) Notice: Subject to any disclaimer, the term of this patent is extended or adjusted under 35 U.S.C. 154(b) by 70 days.

(21) Appl. No.: 11/296,564

(22) Filed: Dec. 8, 2005

(65) Prior Publication Data

US 2007/0135439 A1 Jun. 14, 2007

(51) Int. Cl.
*A61K 31/535* (2006.01)
*C07D 487/04* (2006.01)
(52) U.S. Cl. ...................... 514/243; 544/184
(58) Field of Classification Search ............... None
See application file for complete search history.

(56) References Cited

FOREIGN PATENT DOCUMENTS

WO      WO 02/02562 A2 *   1/2002

\* cited by examiner

*Primary Examiner*—Rebecca L Anderson
*Assistant Examiner*—Michael P Barker
(74) *Attorney, Agent, or Firm*—B. Aaron Schulman; Stites & Harbison PLLC

(57) ABSTRACT

The present invention concerns new compounds of formula (I), their process of preparation and their therapeutic use.

9 Claims, No Drawings

INHIBITORS OF CYSTEINE PROTEASES, THE PHARMACEUTICAL COMPOSITIONS THEREOF AND THEIR THERAPEUTIC APPLICATIONS

The present invention concerns new inhibitors of cysteine proteases, their process of preparation and their therapeutic use.

Proteases can be categorized based on their substrate specificities or mechanisms of catalysis. Upon the basis of the mechanism of peptide hydrolysis, five major protease classes are known: serine, cysteine, aspartic, threonine and metalloproteases. Cysteine proteases comprise, inter allia, de-ubiquitination enzymes, caspases, cathepsins, calpains as well as viral, bacterial or parasitic cysteine proteases.

De-ubiquitination enzymes include Ubiquitin Specific Proteases (USPs) and Ubiquitin Carboxy Hydrolases (UCHs). Broadly speaking, the ubiquitin pathway regulates protein degradation and is more particularly involved in cancer, in neurodegenerative diseases such as Alzheimer's disease, Parkinson's disease, in inflammation, in viral infectivity and latency (in particular for Herpes simplex virus-1, Epstein-Barr virus, SARS coronavirus), or in cardiovascular diseases (*Chem. Rev.* 1997, 97, p. 133-171; *Chem. Rev.* 2002, 102, p. 4459-4488; *J. Biochem.* 2003, 134, p. 9-18; *J. Virology,* 2005, 79(7), p. 4550-4551; *Cardiovasc. Res.* 2004, 61, p. 11-21).

Caspases have been shown to be involved in apoptosis and hence are targets in hepatitis, liver failure, inflammation, cardiac ischemia and failure, renal failure, neurodegeneration, deafness, diabetes, or stroke (*J. Pharmacol Exp. Ther.,* 2004, 308(3), p. 1191-1196, *J. Cell. Physiol.,* 2004, 200(2), p. 177-200; *Kidney Int,* 2004, 66(2), p. 500-506; *Am. J. Pathol.,* 2004, 165(2), p. 353-355; *Mini Rev. Chem.,* 2004, 4(2), p. 153-165; *Otol. Neurotol.,* 2004, 25(4), p. 627-632; Ref. 7, 21, 22, 23, 24, 25).

Cathepsins generally have been shown to be involved in cancer and metastasis, inflammation, immunology/immunoregulation (*Eur. Respir. J.,* 2004, 23(4), p. 620-628) and atherosclerosis (*Ageing Res. Rev.* 2003, 2(4), p. 407-418). More particularly, cathepsins include cathepsin B and B-like which are implicated in cancer and metastasis, and arthritis (*Cancer Metastasis Rev.,* 2003, 22(2-3), p. 271-286; *Biol. Chem.,* 2003, 384(6), p. 845-854 and *Biochem. Soc. Symp.,* 2003, 70, p. 263-276), cathepsin D, involved in particular in cancer and metastasis (*Clin. Exp. Metastasis,* 2004, 21(2), p. 91-106), cathepsin K acting in osteoporosis and arthritis (*Int. J. Pharm.,* 2004, 277(1-2), p. 73-79), cathepsin S which has been shown to play a role in antigen presentation in immunology (*Drug News Perspective,* 2004, 17(6), p. 357-363).

Calpains play a role in ageing in general (*Ageing Res. Rev.* 2003, 2(4), p. 407-418), as well as diabetes (*Mol. Cell. Biochem.,* 2004, 261(1), p. 161-167) and cataract (*Trends Mol. Med.,* 2004, 10(2), p. 78-84) more particularly.

Viral cysteine proteases have been identified in rhinoviruses, poliomyelitis virus, hepatitis A virus, hepatitis C virus, adenovirus, or SARS coronavirus (*Chem. Rev.* 1997, 97, p. 133-171; *Chem. Rev.* 2002. 102, p. 4459-4488 *J. Virology,* 2005, 79(7), p. 4550-4551 and *Acta Microbiol. Immunol. Hung.,* 2003, 50(1), p. 95-101).

Bacterial cysteine proteases include streptopain, staphylococcal cysteine protease, clostripain or gingipains; yeasts such as *Aspergillus flavus* have also been shown to express cysteine proteases which may constitute a virulence factor (*Chem. Rev.* 1997, 97, p; 133-171).

Parasitic cysteine proteases have been reviewed in *Molecular & Biochemical Parasitology* (2002, 120, p. 1-21) and *Chem. Rev.* (2002, 102, p. 4459-4488) for example. It is worth noting that the parasitic agents responsible for most major parasitic diseases are making use of their own cysteine proteases at some point or another of their infective, nutritive or reproductive cycles; such diseases include malaria, Chagas' disease, African trypanosomiasis, leishmaniasis, giardiasis, trichomoniasis, amoebiasis, crypto-sporidiasis, toxoplamiasis, schistosomiasis, fasciolasis, onchocercosis, and other infections by some other flat or round worms.

Therefore, identifying a novel class of inhibitors of cysteine proteases is of significant importance in a wide range of diseases and pathological conditions.

U.S. Pat. No. 6,514,927, WO01/79209 and WO02/02562 disclose compounds comprising 4 fused cycles. However, their use as cysteine protease inhibitors is not suggested.

According to a first object, the present invention concerns a compound of formula (I):

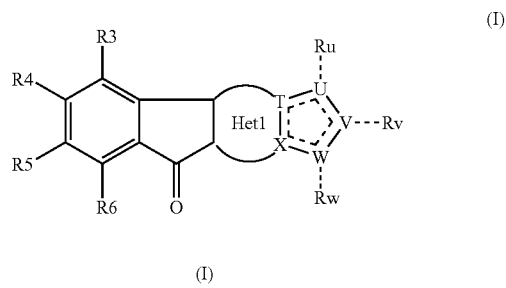

(I)

wherein

──── is either a single or double bond, as appropriate;
▬▬▬ is either none or a single bond, as appropriate;

is a 5 to 7-membered heterocycle, preferably heteroaryl comprising 1 to 5 heteroatoms optionally substituted by one or more substituents chosen from the group consisting in H, CN, =O, Hal, Alk, OAlk, OH, NRCN, C(CN)=C(OH)(OAlk), SR, NRR', C(O)NRR', Heterocycle, Aryle, Heteroaryle, where Alk, Aryle, Heteroaryle, heterocycle are optionally substituted by Hal, NRR', CN, OH, $CF_3$, Aryle, Heteroaryle, OAlk;

where

and

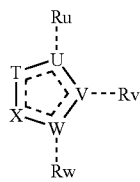

are fused together by T and X;

T, U, V, W, X are the same or different and may be chosen from C, N, O, S.

Ru, Rv, Rw are the same or different and may be chosen from the group consisting in H, CN, =O, Hal, Alk, OAlk, OH, NRCN, C(CN)=C(OH)(OAlk), SR, NRR', C(O)NRR', Heterocycle, Aryle, Heteroaryle, Cycloalkyl where Alk, Aryle, Heteroaryle, heterocycle, Cycloalkyl are optionally substituted by Hal, NRR', CN, OH, CF$_3$, Aryle, Heteroaryle, OAlk, provided that at least one of Ru, Rv, Rw is present and different from H.

Preferably, T, U, V, W, X are C or N.

R3, R4, R5, R6 are each identical or different and are independently chosen from the group consisting in H, OAlk, Alk, Hal, NRR', CN, OH, OCF$_3$, CF$_3$, Aryle, Heteroaryle;

R and R' are each identical or different and are independently chosen from the group consisting in H, Alk, wherein Alk is optionally substituted by Hal, NRR', CN, OH, CF$_3$, Aryle, Heteroaryle;

or their pharmaceutically acceptable salts, hydrates, or hydrated salts, or the polymorphic crystalline structures of these compounds or their optical isomers, racemates, diastereomers or enantiomers, with the exception of 1-Amino-2,3,4,10,10a-pentaaza-cyclopenta[b]fluoren-9-one.

Preferably, (Het1)

contains 2 or 3 heteroatoms; more preferably, 2 or 3 N.

Most preferably, (Het1) is (structures shown) or (structures shown),

Preferably, (Het1) is unsubstituted.

Preferably, (structure with Ru, Rw) is (structure) or (structure)

where Rw or Ru is present and different from H.

Preferably, at least one of Ru, Rv, Rw is chosen from Aryle, Alk, NRR', Hal, -AlkAryl, -AlkOH, -AlkOAlk, Cycloalkyl.

Preferably, R3, R4, R5, R6 are each identical or different and are independently chosen from the group consisting in H, Hal, Alk, OAlk, OCF$_3$.

Preferably, R and R' are each identical or different and are independently chosen from the group consisting in H, Alk.

Preferably, Rv, Rw are either H or absent.

Preferred compounds of formula (I) are those of formula (Ia):

(Ia)

Preferred compounds of the invention are chosen from the group consisting in:

1-Methyl-2,3,4,10,10a-pentaaza-cyclopenta[b]fluoren-9-one

3-Methyl-1,2,3a,4,10-pentaaza-cyclopenta[b]fluoren-9-one

3-Amino-1,2,3a,4,10-pentaaza-cyclopenta[b]fluoren-9-one

1-Ethyl-2,3,4,10,10a-pentaaza-cyclopenta[b]fluoren-9-one

3-Ethyl-1,2,3a,4,10-pentaaza-cyclopenta[b]fluoren-9-one

1-Propyl-2,3,4,10,10a-pentaaza-cyclopenta[b]fluoren-9-one

3-Propyl-1,2,3a,4,10-pentaaza-cyclopenta[b]fluoren-9-one

1-Butyl-2,3,4,10,10a-pentaaza-cyclopenta[b]fluoren-9-one

3-Butyl-1,2,3a,4,10-pentaaza-cyclopenta[b]fluoren-9-one

1-Isobutyl-2,3,4,10,10a-pentaaza-cyclopenta[b]fluoren-9-one

3-Isobutyl-1,2,3a,4,10-pentaaza-cyclopenta[b]fluoren-9-one

1-Hydroxymethyl-2,3,4,10,10a-pentaaza-cyclopenta[b]fluoren-9-one

3-Hydroxymethyl-1,2,3a,4,10-pentaaza-cyclopenta[b]fluoren-9-one

1-Methoxymethyl-2,3,4,10,10a-pentaaza-cyclopenta[b]fluoren-9-one

3-Methoxymethyl-1,2,3a 4,10-pentaaza-cyclopenta[b]fluoren-9-one

1-Cyclopropyl-2,3,4,10,10a-pentaaza-cyclopenta[b]fluoren-9-one

3-Cyclopropyl-1,2,3a,4,10-pentaaza-cyclopenta[b]fluoren-9-one

1-Benzyl-2,3,4,10,10a-pentaaza-cyclopenta[b]fluoren-9-one

3-Benzyl-1,2,3a,4,10-pentaaza-cyclopenta[b]fluoren-9-one

1-Chloro-2,3,4,10,10a-pentaaza-cyclopenta[b]fluoren-9-one

1-Bromo-2,3,4,10,10a-pentaaza-cyclopenta[b]fluoren-9-one 3-bromo-1,2,3a,4,10-pentaaza-cyclopenta[b]fluoren-9-one 6-(7)-Chloro-1-methyl-2,3,4,10,10a-pentaaza-cyclopenta[b]fluoren-9-one 7-Chloro-3-methyl-1,2,3a,4,10-pentaaza-cyclopenta[b]fluoren-9-one 2-Methyl-2H-1,2,3,4,10-pentaaza-cyclopenta[b]fluoren-9-one 2-Benzyl-2H-1,2,3,4,10-pentaaza-cyclopenta[b]fluoren-9-one or their pharmaceutically acceptable salts, hydrates, or hydrated salts, or the polymorphic crystalline structures of these compounds or their optical isomers, racemates, diastereomers or enantiomers.

As used hereabove or hereafter:

Alk represents alkyl, alken or alkyn.

"Alkyl" means an aliphatic hydrocarbon group which may be straight or branched having 1 to 20 carbon atoms in the chain. Preferred alkyl groups have 1 to 12 carbon atoms in the chain. "Branched" means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, octyl, nonyl, decyl.

"Alken" means an aliphatic hydrocarbon group containing a carbon-carbon double bond and which may be straight or branched having 2 to 15 carbon atoms in the chain. Preferred alkenyl groups have 2 to 12 carbon atoms in the chain; and more preferably about 2 to 4 carbon atoms in the chain. Exemplary alkenyl groups include ethenyl, propenyl, n-butenyl, i-butenyl, 3-methylbut-2-enyl, n-pentenyl, heptenyl, octenyl, nonenyl, decenyl.

"Alkyn" means an aliphatic hydrocarbon group containing a carbon-carbon triple bond and which may be straight or branched having 2 to 15 carbon atoms in the chain. Preferred alkynyl groups have 2 to 12 carbon atoms in the chain; and more preferably 2 to 4 carbon atoms in the chain. Exemplary alkynyl groups include ethynyl, propynyl, n-butynyl, 2-butynyl, 3-methylbutynyl, n-pentynyl, heptynyl, octynyl and decynyl.

"Halogen atom" refers to fluorine, chlorine, bromine or iodine atom; preferably fluorine and chlorine atom.

"Aryl" means an aromatic monocyclic or multicyclic hydrocarbon ring system of 6 to 14 carbon atoms, preferably of 6 to 10 carbon atoms. Exemplary aryl groups include phenyl or naphthyl.

As used herein, the terms "heterocycle" or "heterocyclic" refer to a saturated, partially unsaturated or unsaturated, non aromatic stable 3 to 14, preferably 5 to 10 membered mono, bi or multicyclic rings wherein at least one member of the ring is a hetero atom. Typically, heteroatoms include, but are not limited to, oxygen, nitrogen, sulfur, selenium, and phosphorus atoms. Preferable heteroatoms are oxygen, nitrogen and sulfur.

Suitable heterocycles are also disclosed in *The Handbook of Chemistry and Physics*, 76th Edition, CRC Press, Inc., 1995-1996, p. 2-25 to 2-26, the disclosure of which is hereby incorporated by reference.

Preferred non aromatic heterocyclic include, but are not limited to pyrrolidinyl, pyrazolidinyl, imidazolidinyl, oxiranyl, tetrahydrofuranyl, dioxolanyl, tetrahydro-pyranyl, dioxanyl, dioxolanyl, piperidyl, piperazinyl, morpholinyl, pyranyl, imidazolinyl, pyrrolinyl, pyrazolinyl, thiazolidinyl, tetrahydrothiopyranyl, dithianyl, thiomorpholinyl, dihydropyranyl, tetrahydropyranyl, dihydropyranyl, tetrahydro-pyridyl, dihydropyridyl, tetrahydropyrimidinyl, dihydrothiopyranyl, azepanyl, as well as the fused systems resulting from the condensation with a phenyl group.

As used herein, the term "heteroaryl" or aromatic heterocycles refers to a 5 to 14, preferably 5 to 10 membered aromatic hetero, mono-, bi- or multicyclic ring. Examples include pyrrolyl, pyridyl, pyrazolyl, thienyl, pyrimidinyl, pyrazinyl, tetrazolyl, indolyl, quinolinyl, purinyl, imidazolyl, thienyl, thiazolyl, benzothiazolyl, furanyl, benzofuranyl, 1,2,4-thiadiazolyl, isothiazolyl, triazoyl, tetrazolyl, isoquinolyl, benzothienyl, isobenzofuryl, pyrazolyl, carbazolyl, benzimidazolyl, isoxazolyl, pyridyl-N-oxide, as well as the fused systems resulting from the condensation with a phenyl group.

"Alkyl", "cycloalkyl", "alkenyl", "alkynyl", "aryl", "heteroaryl", "heterocycle" and the likes refers also to the corresponding "alkylene", "cycloalkylene", "alkenylene", "alkynylene", "arylene", "heteroarylene", "heterocyclene" and the likes which are formed by the removal of two hydrogen atoms.

As used herein, the term "patient" refers to either an animal, such as a valuable animal for breeding, company or preservation purposes, or preferably a human or a human child, which is afflicted with, or has the potential to be afflicted with one or more diseases and conditions described herein.

As used herein, a "therapeutically effective amount" refers to an amount of a compound of the present invention which is effective in preventing, reducing, eliminating, treating or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment.

As used herein, the term "pharmaceutically acceptable" refers to those compounds, materials, excipients, compositions or dosage forms which are, within the scope of sound medical judgment, suitable for contact with the tissues of human beings and animals without excessive toxicity, irritation, allergic response or other problem complications commensurate with a reasonable benefit/risk ratio.

As used herein, "pharmaceutically acceptable salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, tartaric, citric, methanesulfonic, benzenesulfonic, glucoronic, glutamic, benzoic, salicylic toluenesulfonic, oxalic, fumaric, maleic, lactic and the like. Further addition salts include ammonium salts such as tromethamine, meglumine, epolamine, etc., metal salts such as sodium, potassium, calcium, zinc or magnesium.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The compounds of the general formula (I) having geometrical and stereoisomers are also a part of the invention.

According to a further object, the present invention is also concerned with the process of preparation of the compounds of formula (I).

The compounds and process of the present invention may be prepared in a number of ways well-known to those skilled in the art. The compounds can be synthesized, for example, by application or adaptation of the methods described below, or variations thereon as appreciated by the skilled artisan. The appropriate modifications and substitutions will be readily apparent and well known or readily obtainable from the scientific literature to those skilled in the art.

In particular, such methods can be found in R. C. Larock, *Comprehensive Organic Transformations*, Wiley-VCH Publishers, 1999.

It will be appreciated that the compounds of the present invention may contain one or more asymmetrically substituted carbon atoms, and may be isolated in optically active or racemic forms. Thus, all chiral, diastereomeric, racemic forms, isomeric forms of a structure are intended, unless the specific stereochemistry or isomeric form is specifically indicated. It is well-known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

Additionally, the process of the invention may lead to several regioisomers which are all encompassed by the present invention. Regioisomers are generally isolated by chromatography.

Compounds of the present invention may be prepared by a variety of synthetic routes. The reagents and starting materials are commercially available, or readily synthesized by well-known techniques by one of ordinary skill in the arts. All substituents, unless otherwise indicated, are as previously defined.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *Protective Groups in Organic Chemistry*, 3$^{rd}$ ed., John Wiley and Sons, 1999; J. F. W. McOmie in *Protective Groups in Organic Chemistry*, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, triethylamine, alkali metal hydrides, such as sodium hydride and potassium hydride; alkyllithium compounds, such as methyllithium and butyllithium; and alkali metal alkoxides, such as sodium methoxide and sodium ethoxide.

Usually, reactions are carded out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, benzene, toluene and xylene; amides, such as dimethylformamide; alcohols such as ethanol and methanol and ethers, such as diethyl ether and tetrahydrofuran.

The reactions can take place over a wide range of temperatures. In general, it is found convenient to carry out the reaction at a temperature of from 0° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The compound thus prepared may be recovered from the reaction mixture by conventional means. For example, the compounds may be recovered by distilling off the solvent from the reaction mixture or, if necessary after distilling off the solvent from the reaction mixture, pouring the residue into water followed by extraction with a water-immiscible organic solvent and distilling off the solvent from the extract. Additionally, the product can, if desired, be further purified by various well-known techniques, such as recrystallization, reprecipitation or the various chromatography techniques, notably column chromatography or preparative thin layer chromatography.

The process of preparation of a compound of formula (I) of the invention is a further object of the present invention.

According to a first aspect, compounds of the invention of formula (I) can be obtained from reacting corresponding compounds of formula (II) and (III):

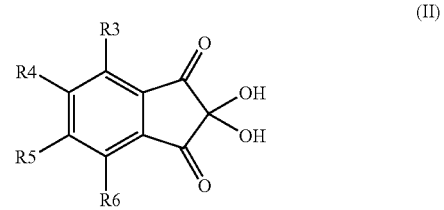

(II)

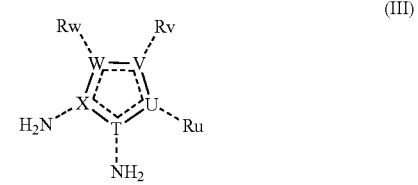

(III)

wherein R3, R4, R5, R6, T, U, V, W, X, Ru, Rv, Rw are defined as in formula (I).

Generally, the reaction is carried out in an organic protic solvent, such as an alcohol (preferably ethanol), in the presence of an acid such as acetic acid.

Alternatively and/or cumulatively, compounds of formula (I) may be obtained from corresponding compounds of formula (I'):

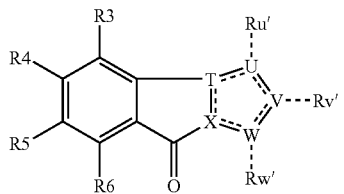

wherein R3, R4, R5, R6, T, U, V, W, X, Ru, Rv, Rw are defined as in formula (I), wherein at least one of Ru', Rv', Rw' is a precursor group of corresponding Ru, Rv, Rw, by one or more step allowing a precursor group to be transformed into the desired Ru, Rv or Rw group.

According to the present invention, the expression "precursor group" of a functional group refers to any group which can, by one or more reactions, lead to the desired function, by means of one or more suitable reagents. Those reactions include de-protection, as well as usual addition, substitution or functionalization reactions.

Compounds of formula (I') may be obtained from corresponding compounds of formula (II) and (III) as discussed above.

The above reactions can be carried out by the skilled person by applying or adapting the methods illustrated in the examples hereinafter.

Further, the process of the invention may also comprise the additional step of isolating the compound of formula (I). This can be done by the skilled person by any of the known conventional means, such as the recovery methods described above.

The starting products (II) and (III) are commercially available or may be obtained by applying or adapting any known methods or those described in the examples.

The synthesis may also be carried out in one pot as a multicomponent reaction.

According to a further object, the present invention concerns also the pharmaceutical compositions comprising a compound of formula (I) as defined below:

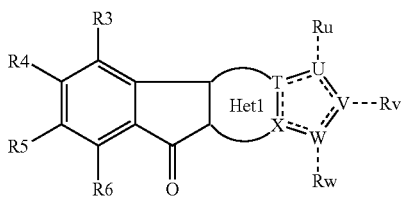

wherein

---- is either a single or double bond, as appropriate;
------ is either none or a single bond, as appropriate;

is a 5 to 7-membered heterocycle, preferably heteroaryl comprising 1 to 5 heteroatoms optionally substituted by one or more substituents chosen from the group consisting in H, CN, =O, Hal, Alk, OAlk, OH, NRCN, C(CN)=C(OH)(OAlk), SR, NRR', C(O)NRR', Heterocycle, Aryle, Heteroaryle, where Alk, Aryle, Heteroaryle, heterocycle are optionally substituted by Hal, NRR', CN, OH, CF$_3$, Aryle, Heteroaryle, OAlk;

where

and

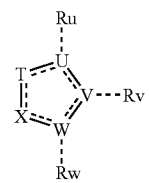

are fused together by T and X;

T, U, V, W, X are the same or different and may be chosen from C, N, O, S.

Ru, Rv, Rw are the same or different and may be chosen from the group consisting in H, CN, =O, Hal, Alk, OAlk, OH, NRCN, C(CN)=C(OH)(OAlk), SR, NRR', C(O)NRR', Heterocycle, Aryle, Heteroaryle, Cycloalkyl where Alk, Aryle, Heteroaryle, heterocycle, Cycloalkyl are optionally substituted by Hal, NRR', CN, OH, CF$_3$, Aryle, Heteroaryle, OAlk, provided that at least one of Ru, Rv, Rw is present and different from H.

Preferably, T, U, V, W, X are C or N.

R3, R4, R5, R6 are each identical or different and are independently chosen from the group consisting in H, OAlk, Alk, Hal, NRR', CN, OH, OCF$_3$, CF$_3$, Aryle, Heteroaryle;

R and R' are each identical or different and are independently chosen from the group consisting in H, Alk, wherein Alk is optionally substituted by Hal, NRR', CN, OH, CF$_3$, Aryle, Heteroaryle;

or their pharmaceutically acceptable salts, hydrates, or hydrated salts, or the polymorphic crystalline structures of these compounds or their optical isomers, racemates, diastereomers or enantiomers.

Preferred embodiments of formula (I) are as defined above in respect of the compounds of the invention.

Preferred compounds for the therapeutic use according to the invention are chosen from the group consisting in:

1-Methyl-2,3,4,10,10a-pentaaza-cyclopenta[b]fluoren-9-one
3-Methyl-1,2,3a,4,10-pentaaza-cyclopenta[b]fluoren-9-one
1-Amino-2,3,4,10,10a-pentaaza-cyclopenta[b]fluoren-9-one.
3-Amino-1,2,3a,4,10-pentaaza-cyclopenta[b]fluoren-9-one
1-Ethyl-2,3,4,10,10a-pentaaza-cyclopenta[b]fluoren-9-one
3-Ethyl-1,2,3a,4,10-pentaaza-cyclopenta[b]fluoren-9-one 1-Propyl-2,3,4,10,10a-pentaaza-cyclopenta[b]fluoren-9-one
3-Propyl-1,2,3a,4,10-pentaaza-cyclopenta[b]fluoren-9-one
1-Butyl-2,3,4,10,10a-pentaaza-cyclopenta[b]fluoren-9-one
3-Butyl-1,2,3a,4,10-pentaaza-cyclopenta[b]fluoren-9-one
1-Isobutyl-2,3,4,10,10a-pentaaza-cyclopenta[b]fluoren-9-one
3-Isobutyl-1,2,3a,4,10-pentaaza-cyclopenta[b]fluoren-9-one
1-Hydroxymethyl-2,3,4,10,10a-pentaaza-cyclopenta[b]fluoren-9-one
3-Hydroxymethyl-1,2,3a,4,10-pentaaza-cyclopenta[b]fluoren-9-one
1-Methoxymethyl-2,3,4,10,10a-pentaaza-cyclopenta[b]fluoren-9-one
3-Methoxymethyl-1,2,3a,4,10-pentaaza-cyclopenta[b]fluoren-9-one
1-Cyclopropyl-2,3,4,10,10a-pentaaza-cyclopenta[b]fluoren-9-one
3-Cyclopropyl-1,2,3a,4,10-pentaaza-cyclopenta[b]fluoren-9-one
1-Benzyl-2,3,4,10,10a-pentaaza-cyclopenta[b]fluoren-9-one
3-Benzyl-1,2,3a,4,10-pentaaza-cyclopenta[b]fluoren-9-one
1-Chloro-2,3,4,10,10a-pentaaza-cyclopenta[b]fluoren-9-one
1-Bromo-2,3,4,10,10a-pentaaza-cyclopenta[b]fluoren-9-one
3-bromo-1,2,3a,4,10-pentaaza-cyclopenta[b]fluoren-9-one
6-(7)-Chloro-1-methyl-2,3,4,10,10a-pentaaza-cyclopenta[b]fluoren-9-one
7-Chloro-3-methyl-1,2,3a,4,10-pentaaza-cyclopenta[b]fluoren-9-one
2-Methyl-2H-1,2,3,4,10-pentaaza-cyclopenta[b]fluoren-9-one
2-Benzyl-2H-1,2,3,4,10-pentaaza-cyclopenta[b]fluoren-9-one or their pharmaceutically acceptable salts, hydrates, or hydrated salts, or the polymorphic crystalline structures of these compounds or their optical isomers, racemates, diastereomers or enantiomers.

According to a still further object, the present invention concerns the use of a compound of formula (I), as defined above in respect of the pharmaceutical composition, for the preparation of a medicament for inhibiting cysteine protease.

The compounds of the invention are useful for inhibiting cysteine proteases, in particular de-ubiquitination enzymes (such as USPs and UCHs), caspases, cathepsins (in particular cathepsin B, D, K, S and the like), calpains as well as viral, bacterial or parasitic cysteine proteases in patients in the need thereof.

The compounds of the invention are particularly useful for treating and/or preventing cancer and metastasis, more particularly prostate and/or colon cancers, neurodegenerative diseases such as Alzheimer's disease and Parkinson's disease, deafness, disorders associated with ageing, inflammatory disorders, arthritis, osteoporosis, hepatitis, liver failure, cardiac ischemia and failure, stroke, atherosclerosis, renal failure, diabetes, cataract; viral acute or latent infections by Herpes simplex virus-1, Epstein-Barr virus, SARS coronavirus, rhinoviruses, poliomyelitis virus, hepatitis A virus, hepatitis C virus, adenoviruses, and the like; bacterial or fungal infections by pathogenic agents belonging to the *Streptococcus* sp., *Staphylococcus* sp., *Clostidium* sp., *Aspergillus* sp., genera and the like; protozoal infections by species members of the *Trypanosoma* sp., *Plasmodium* sp., *Leishmania* sp., *Trichomonas* sp., *Entamoeba* sp., *Giardia* sp., *Toxoplasma* sp., *Cryptosporidium* sp., genera and the like; flat or round worm infections by species members of the *Fasciola* sp., *Schistosoma* sp., *Onchocerca* sp., *Ascaris* sp., *Taenia* sp., *Caenorhabitis* sp., *Toxocara* sp., *Haemonchus* sp., *Ancylostoma* sp., *Trichuris* sp., *Trichinella* sp., *Strongyloides* sp., *Brugia* sp., genera and the like; as well as immunological, immunoregulatory or antigen presentation disorders.

The present invention also concerns the corresponding methods of treatment comprising the administration of a compound of the invention together with a pharmaceutically acceptable carrier or excipient to a patient in the need thereof.

The identification of those subjects who are in need of treatment of herein-described diseases and conditions is well within the ability and knowledge of one skilled in the art. A veterinarian or a physician skilled in the art can readily identify, by the use of clinical tests, physical examination, medical/family history or biological and diagnostic tests, those subjects who are in need of such treatment.

A therapeutically effective amount can be readily determined by the attending diagnostician, as one skilled in the art, by the use of conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

The amount of a compound of formula (I), which is required to achieve the desired biological effect, will vary depending upon a number of factors, including the chemical characteristics (e.g. hydrophobicity) of the compounds employed, the potency of the compounds, the type of disease, the species to which the patient belongs, the diseased state of the patient, the route of administration, the bioavailability of the compound by the chosen route, all factors which dictate the required dose amounts, delivery and regimen to be administered.

"Pharmaceutically" or "pharmaceutically acceptable" refer to molecular entities and compositions that do not produce an adverse, allergic or other untoward reaction when administered to an animal, or a human, as appropriate.

As used herein, "pharmaceutically acceptable excipient" includes any carriers, diluents, adjuvants, or vehicles, such as preserving or antioxidant agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well-known in the art. Except insofar as any conventional media or agent is incompatible with the active ingredient, its use in the therapeutic compositions is contemplated. Supplementary active ingredients can also be incorporated into the compositions as suitable therapeutic combinations.

In the context of the invention, the term "treating" or "treatment", as used herein, means reversing, alleviating, inhibiting the progress of, or preventing the disorder or condition to which such term applies, or one or more symptoms of such disorder or condition.

"Therapeutically effective amount" means an amount of a compound/medicament according to the present invention effective in preventing or treating a pathological condition requiring the inhibition of an active cysteine protease involved in its pathogenesis.

According to the invention, the term "patient", or "patient in need thereof", is intended for an animal or a human being affected or likely to be affected with a pathological condition involving an active cysteine protease in its pathogenesis. Preferably, the patient is human.

In general terms, the compounds of this invention may be provided in an aqueous physiological buffer solution containing 0.1 to 10% w/v compound for parenteral administration. Typical dose ranges are from 1 µg/kg to 0.1 g/kg of body weight per day; a preferred dose range is from 0.01 mg/kg to 10 mg/kg of body weight per day or an equivalent dose in a human child. The preferred dosage of drug to be administered is likely to depend on such variables as the type and extent of progression of the disease or disorder, the overall health status of the particular patient, the relative biological efficacy of the compound selected, the formulation of the compound, the route of administration (intravenous, intramuscular, or other), the pharmacokinetic properties of the compound by the chosen delivery route, and the speed (bolus or continuous infusion) and schedule of administrations (number of repetitions in a given period of time).

The compounds of the present invention are also capable of being administered in unit dose forms, wherein the term "unit dose" means a single dose which is capable of being administered to a patient, and which, can be readily handled and packaged, remaining as a physically and chemically stable unit dose comprising either the active compound itself; or as a pharmaceutically acceptable composition, as described hereinafter. As such, typical total daily dose ranges are from 0.01 to 100 mg/kg of body weight. By way of general guidance, unit doses for humans range from 1 mg to 3000 mg per day. Preferably, the unit dose range is from 1 to 500 mg administered one to six times a day, and even more preferably from 10 mg to 500 mg, once a day. Compounds provided herein can be formulated into pharmaceutical compositions by admixture with one or more pharmaceutically acceptable excipients. Such unit dose compositions may be prepared for use by oral administration, particularly in the form of tablets, simple capsules or soft gel capsules; or intranasally, particularly in the form of powders, nasal drops, or aerosols; or dermally, for example, topically in ointments, creams, lotions, gels or sprays, or via trans-dermal patches.

The compositions may conveniently be administered in unit dosage form and may be prepared by any of the methods well-known in the pharmaceutical art, for example, as described in Remington: The Science and Practice of Pharmacy, 20$^{th}$ ed.; Gennaro, A. R., Ed.; Lippincott Williams & Wilkins: Philadelphia, Pa., 2000.

Preferred formulations include pharmaceutical compositions in which a compound of the present invention is formulated for oral or parenteral administration.

For oral administration, tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolve, modified-release or sustained-release preparations and formulations, and wherein such sustained-release formulations are preferably bi-modal. Preferred tablets contain lactose, cornstarch, magnesium silicate, croscarmellose sodium, povidone, magnesium stearate, or talc in any combination.

Liquid preparations for parenteral administration include sterile aqueous or non-aqueous solutions, suspensions, and emulsions. The liquid compositions may also include binders, buffers, preservatives, chelating agents, sweetening, flavoring and coloring agents, and the like. Non-aqueous solvents include alcohols, propylene glycol, polyethylene glycol, vegetable oils such as olive oil, and organic esters such as ethyl oleate. Aqueous carriers include mixtures of alcohols and water, buffered media, and saline. In particular, biocompatible, biodegradable lactide polymer, lactide/glycolide copolymer, or polyoxyethylene-polyoxypropylene copolymers may be useful excipients to control the release of the active compounds. Intravenous vehicles can include fluid and nutrient replenishers, electrolyte replenishers, such as those based on Ringer's dextrose, and the like. Other potentially useful parenteral delivery systems for these active compounds include ethylene-vinyl acetate copolymer particles, osmotic pumps, implantable infusion systems, and liposomes.

Alternative modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations. Formulations suitable for transdermal administration can be presented as discrete patches and can be lipophilic emulsions or buffered, aqueous solutions, dissolved and/or dispersed in a polymer or an adhesive.

The invention is further illustrated but not restricted by the description in the following examples.

Representative compounds of the invention are summarized in the table below:

| Formula | Preparation procedure |
|---|---|
| (structure) | Example 1b/A |
| (structure) | Example 1b/B |
| (structure) | Example 1c |
| (structure) | Example 1c/A |
| (structure) | Example 1c/B |
| (structure) | Example 1d/A |
| (structure) | Example 1d/B |
| (structure) | Example 1e/A |
| (structure) | Example 1e/B |
| (structure) | Example 1f/A |
| (structure) | Example 1f/B |
| (structure) | Example 1g/A |
| (structure) | Example 1g/B |
| (structure) | Example 1h/A |

-continued
| Formula | Preparation procedure |
|---|---|
| 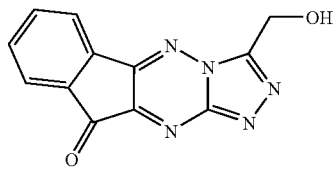 | Example 1h/B |
| 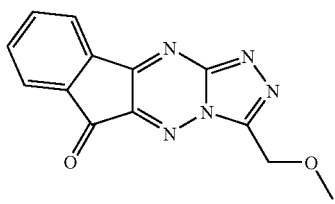 | Example 1i/A |
| 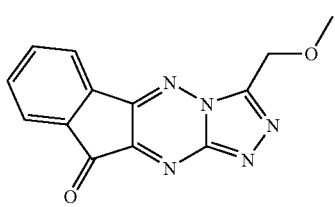 | Example 1i/B |
| 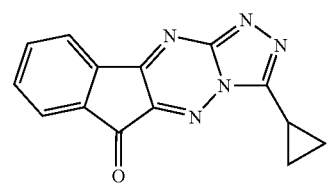 | Example 1j/A |
| 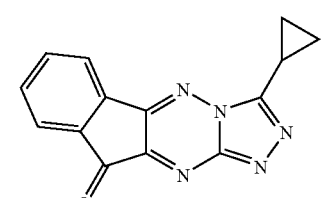 | Example 1j/B |
| 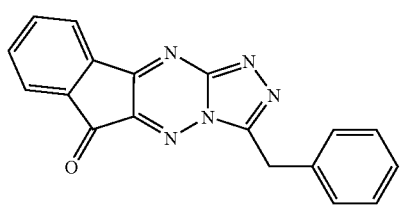 | Example 1k/A |
| 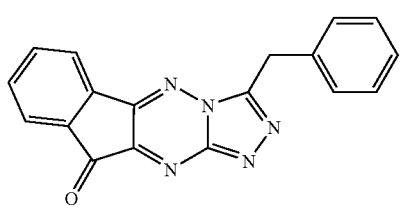 | Example 1k/B |
-continued
| Formula | Preparation procedure |
|---|---|
| 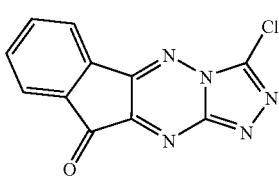 | Example 2a/A |
| 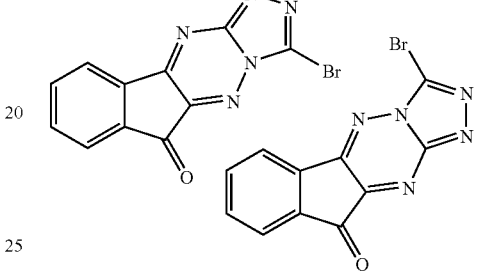 | Example 2b |
| 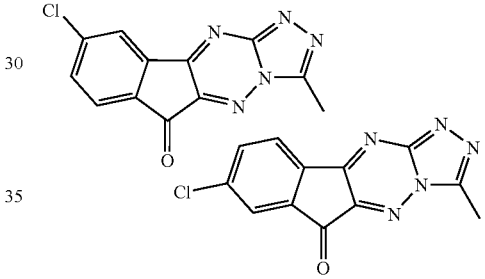 | Example 3/A |
| 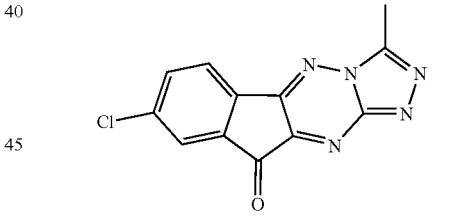 | Example 3/B |
| 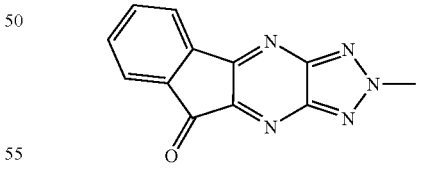 | Example 4a |
| 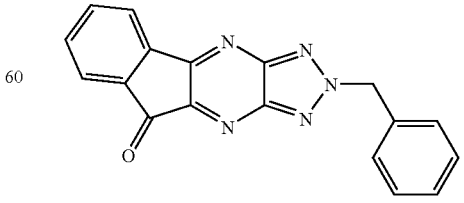 | Example 4b |

EXPERIMENTAL

Representative compounds of the invention can be synthesized according to the following procedures:

General procedure A: synthesis of pentaaza-cyclopenta[b]fluoren-9-one

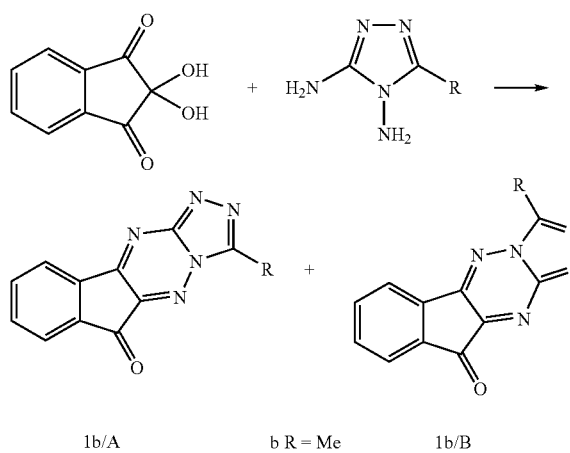

1b/A      b R = Me      1b/B

A mixture of substituted (1,2,4)-triazole-3,4-diamine (8.8 mmol) and ninhydrin (1.57 g, 8.8 mmol) in EtOH (10 ml) and AcOH (1.5 ml) was refluxed for 2-16 hours. The solvent was removed under reduced pressure and the residue was dissolved in EtOAc, washed with saturated $K_2CO_3$ and brine. The organic phase was dried over $Na_2SO_4$, filtered and the solvents removed by evaporation under reduced pressure. The crude was purified as follows: silica gel flash chromatography (toluene/MeOH 95:5 to 8:2 or $CH_2Cl_2$/EtOAc 9:1 to 1:1) for the purification of the regioisomeric mixture, then neutral alumina (grade II) flash chromatography ($CH_2Cl_2$/EtOAc 7:3 to $CH_2Cl_2$/MeOH 1:1+5% HCOOH or AcOH) for the separation of the regioisomers.

1-Methyl-2,3,4,10,10a-pentaaza-cyclopenta[b]fluoren-9-one (1b/A)

Prepared according to the general procedure A in 13% yield as yellow solid.

$^1$H NMR (300 MHz, DMSO d$_6$): δ 8.23 (d, 1H), 8.02 (m, 2H), 7.89 (ddd, 1H), 2.72 (s, 3H). ESI$^+$MS: calcd for $C_{12}H_7N_5O$: 237.22; found: 238.2 (MH$^+$).

3-Methyl-1,2,3a,4,10-pentaaza-cyclopenta[b]fluoren-9-one (1b/B)

Prepared according to the general procedure A in 30% yield as yellow solid.

$^1$H NMR (300 MHz, DMSO d$_6$): δ 8.16 (d, 1H), 8.05-7.95 (m, 2H), 7.85 (ddd, 1H), 2.77 (s, 3H). ESI$^+$MS: calcd for $C_{12}H_7N_5O$: 237.22; found: 238.2 (MH$^+$).

Synthesis of amino-pentaaza-cyclopenta[b]fluoren-9-one (1c)

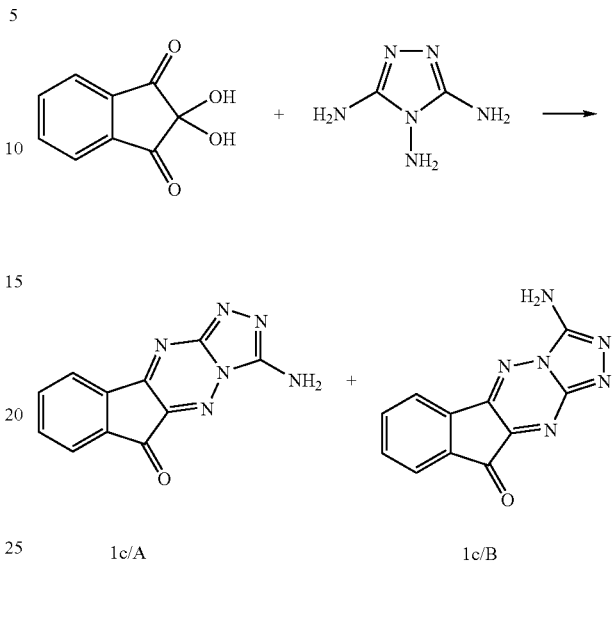

1c/A      1c/B

A mixture of (1,2,4)-triazole-3,4,5-triamine (2.5 g, 21.9 mmol) in 1:1 AcOH/H$_2$O (80 ml) was heated to 70° C. Ninhydrin (3.9 g, 21.9 mmol) was dissolved in 1:1 AcOH/H$_2$O (80 ml), heated at 50° C. and subsequently added to the triamine solution. The reaction was heated at 70° C. for 3 hours and then stirred overnight at room temperature. The mixture was cooled to 0° C. and stirred for 1 hour. The precipitate was collected by filtration, washed with cold water and GIBSON dried under vacuum, leading to 3,9 g of 1c as regioisomeric mixture (6:4 ratio, 82% yield). The regioisomers were separated following the General procedure A.

1-Amino-2,3,4,10,10a-pentaaza-cyclopenta[b]fluoren-9-one (1c/A)

Red solid. $^1$H NMR (300 MHz, DMSO d$_6$): δ 8.15 (d, 1H), 8.01-7.95 (m, 2H), 7.83 (ddd, 1H), 6.98 (s, 2H). ESI$^+$MS: calcd for $C_{11}H_6N_6O$: 238.21; found: 239.1 (MH$^+$).

3-Amino-1,2,3a,4,10-pentaaza-cyclopenta[b]fluoren-9-one (1c/B)

Brown solid. $^1$H NMR (300 MHz, DMSO d$_6$): δ 8.05-7.93 (m, 3H), 7.82 (ddd, 1H), 7.14 (s, 2H). ESI$^+$MS: calcd for $C_{11}H_6N_6O$: 238.21; found: 239.1 (MH$^+$).

General procedure B: synthesis of pentaaza-cyclopenta[b]fluoren-9-one

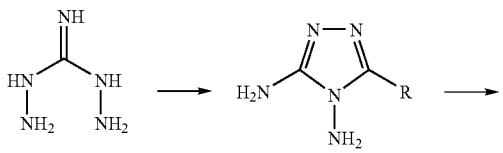

-continued

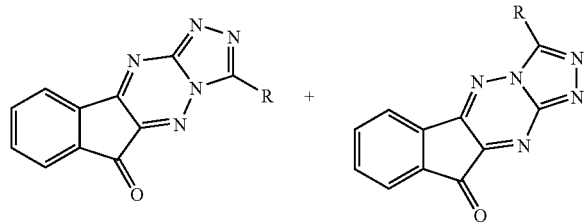

1d-I/A d R = Et
e R = Pr
f R = Bu
g R = iBu
h R = ―CH$_2$OH
i R = ―CH$_2$OCH$_3$
j R = cyclopropyl
k R = Bn 1d-I/B The preparation of diaminotriazoles follows the procedure reported in *Eur. J. Med. Chem.-Chim. Ther.* 1986, 21, 235.

A mixture of diaminoguanidine hydrochloride (1 g, 8 mmol) in an excess (10 g) of the appropriate carboxylic acid was stirred and heated at 120-130° C. for 12-24 hours. The solution was cooled to room temperature and HCl 37% (10 ml) was added. The mixture was refluxed for 2-3 hours and then concentrated to dryness in vacuo. The obtained crude was washed with Et$_2$O (×3) and used without any further purification.

For the condensation between the crude diaminotriazole and ninhydrin, see the General procedure A.

1-Ethyl-2,3,4,10,10a-pentaaza-cyclopenta[b]fluoren-9-one (1d/A)

Prepared according to the general procedure B in 48% yield as yellow solid.

$^1$H NMR (300 MHz, CDCl$_3$): δ 8.21 (d, 1H), 8.00 (d, 1H), 7.90 (ddd, 1H), 7.77 (ddd, 1H), 3.21 (q, 2H), 1.49 (t, 3H). ESI$^+$MS: calcd for C$_{13}$H$_9$N$_5$O: 251.25; found: 252.1 (MH$^+$).

3-Ethyl-1,2,3a,4,10-pentaaza-cyclopenta[b]fluoran-9-one (1d/B)

Prepared according to the general procedure B in 32% yield as yellow solid. $^1$H NMR (300 MHz, CDCl$_3$): δ 8.12 (d, 1H), 8.02 (d, 1H), 7.88 (ddd, 1H), 7.75 (ddd, 1H), 3.25 (q, 2H), 1.53 (t, 3H). ESI$^+$MS: calcd for C$_{13}$H$_9$N$_5$O: 251.25; found: 252.1 (MH$^+$).

1-Propyl-2,3,4,10,10a-pentaaza-cyclopenta[b]fluoren-9-one (1e/A)

Prepared according to the general procedure B in 14% yield as yellow solid.

$^1$H NMR (300 MHz, CDCl$_3$): δ 8.18 (d, 1H), 7.97 (d, 1H), 7.87 (ddd, 1H), 7.75 (ddd, 1H), 3.12 (dd, 2H), 1.91 (m, 2H), 1.01 (t, 3H). ESI$^+$MS: calcd for C$_{14}$H$_{11}$N$_5$O: 265.28; found: 266.2 (MH$^+$).

3-Propyl-1,2,3a,4,10-pentaaza-cyclopenta[b]fluoren-9-one (1e/B)

Prepared according to the general procedure B in 12% yield as yellow solid.

$^1$H NMR (300 MHz, CDCl$_3$): δ 8.10 (ddd, 1H), 8.00 (ddd, 1H), 7.86 (ddd, 1H), 7.74 (ddd, 1H), 3.19 (dd, 2H), 1.96 (m, 2H), 1.06 (t, 3H). ESI$^+$MS: calcd for C$_{14}$H$_{11}$N$_5$O: 265.28; found: 266.2 (MH$^+$).

1-Butyl-2,3,4,10,10a-pentaaza-cyclopenta[b]fluoren-9-one (1f/A)

Prepared according to the general procedure B in 6% yield as yellow solid.

$^1$H NMR (300 MHz, DMSO d$_6$): δ 8.23 (d, 1H), 8.02 (m, 2H), 7.89 (ddd, 1H), 3.10 (dd, 2H), 1.81 (m, 2H), 1.42 (m, 2H), 0.94 (t, 3H). ESI$^+$MS: calcd for C$_{15}$H$_{13}$N$_5$O: 279.30; found: 280.2 (MH$^+$).

3-Butyl-1,2,3a,4,10-pentaaza-cyclopenta[b]fluoren-9-one (1f/B)

Prepared according to the general procedure B in 10% yield as yellow solid.

$^1$H NMR (300 MHz, DMSO d$_6$): δ 8.16 (d, 1H), 7.99 (m, 2H), 7.85 (dd, 1H), 3.16 (dd, 2H), 1.87 (m, 2H), 1.44 (m, 2H), 0.96 (t, 3H). ESI$^+$MS: calcd for C$_{15}$H$_{13}$N$_5$O: 279.30; found: 280.3 (MH$^+$).

1-Isobutyl-2,3,4,10,10a-pentaaza-cyclopenta[b]fluoren-9-one (1g/A)

Prepared according to the general procedure B in 17% yield as yellow solid.

$^1$H NMR (300 MHz, CDCl$_3$): δ 8.20 (d, 1H), 7.99 (d, 1H), 7.89 (ddd, 1H), 7.76 (ddd, 1H), 3.06 (d, 2H), 2.34 (m, 1H), 1.00 (d, 6H). ESI$^+$MS: calcd for C$_{15}$H$_{13}$N$_5$O: 279.30; found: 280.2 (MH$^+$).

3-Isobutyl-1,2,3a,4,10-pentaaza-cyclopenta[b]fluoren-9-one (1g/B)

Prepared according to the general procedure B in 12% yield as yellow solid.

$^1$H NMR (300 MHz, CDCl$_3$): δ 8.10 (d, 1H), 7.99 (d, 1H), 7.86 (ddd, 1H), 7.74 (ddd, 1H), 3.11 (d, 2H), 2.38 (m, 1H), 1.04 (d, 6H). ESI$^+$MS: calcd for C$_{15}$H$_{13}$N$_5$O: 279.30; found: 280.2 (MH$^+$).

1-Hydroxymethyl-2,3,4,10,10a-pentaaza-cyclopenta[b]fluoren-9-one (1h/A)

Prepared according to the general procedure B in 10% yield as yellow solid.

$^1$H NMR (300 MHz, DMSO d$_6$): δ 8.24 (d, 1H), 8.02 (m, 2H), 7.90 (ddd, 1H), 5.85 (t, 1H), 4.92 (d, 2H). ESI$^+$MS: calcd for C$_{12}$H$_7$N$_5$O$_2$: 253.22; found: 254.1 (MH$^+$).

3-Hydroxymethyl-1,2,3,4,10-pentaaza-cyclopenta[b]fluoren-9 one (1h/B)

Prepared according to the general procedure B in 1% yield as brown solid.

$^1$H NMR (300 MHz, DMSO d$_6$): δ 8.15 (d, 1H), 8:06-7.96 (m, 2H), 7.86 (ddd, 1H), 5.84 (t, 1H), 4.98 (d, 2H). ESI$^+$MS: calcd for C$_{12}$H$_7$N$_5$O$_2$: 253.22; found: 254.2 (MH$^+$).

1-Methoxymethyl-2,3,4,10,10a-pentaaza-cyclopenta[b]fluoren-9-one (1i/A)

Prepared according to the general procedure B in 2% yield as yellow solid.

$^1$H NMR (300 MHz, CDCl$_3$): δ 8.18 (ddd, 1H), 7.96 (ddd, 1H), 7.87 (ddd, 1H), 7.75 (ddd, 1H), 4.92 (s, 2H), 3.42 (s, 3H). ESI$^+$MS: calcd for C$_{13}$H$_9$N$_5$O$_2$: 267.25; found: 268.1 (MH$^+$).

3-Methoxymethyl-1,2,3a,4,10-pentaaza-cyclopenta[b]fluoren-9-one (1j/B)

Prepared according to the general procedure B in 2% yield as brown solid.

$^1$H NMR (300 MHz, CDCl$_3$): δ 8.13 (d, 1H), 8.01 (d, 1H), 7.87 (ddd, 1H), 7.76 (ddd, 1H), 5.02 (s, 2H), 5.49 (s, 3H). ESI$^+$MS: calcd for C$_{13}$H$_9$N$_5$O$_2$: 267.25; found: 268.1 (MH$^+$).

1-Cyclopropyl-2,3,4,10,10a-pentaaza-cyclopenta[b]fluoren-9-one (1j/A)

Prepared according to the general procedure B in 6% yield as yellow solid. $^1$H NMR (300 MHz, CDCl$_3$): δ 8.25 (dd, 1H), 8.04 (dd, 1H), 7.93 (ddd, 1H), 7.80 (ddd, 1H), 2.51 (m, 1H), 1.44 (m, 2H), 1.26 (m, 2H). ESI$^+$MS: calcd for C$_{14}$H$_9$N$_5$O: 263.26; found: 264.2 (MH$^+$).

3-Cyclopropyl-1,2,3a,4,10-pentaaza-cyclopenta[b]fluoren-9-one (1j/B)

Prepared according to the general procedure B in 4% yield as yellow solid. $^1$H NMR (300 MHz, CDCl$_3$): δ 8.14 (dd, 1H), 8.05 (dd, 1H), 7.90 (ddd, 1H), 7.78 (ddd, 1H), 2.55 (m, 1H), 1.52 (m, 2H), 1.31 (m, 2H). ESI$^+$MS: calcd for C$_{14}$H$_9$N$_5$O: 263.26; found: 264.1 (MH$^+$).

1-Benzyl-2,3,4,10,10a-pentaaza-cyclopenta[b]fluoren-9-one (1k/A)

Prepared according to the general procedure B in 12% yield as bright yellow solid. $^1$H NMR (300 MHz, CDCl$_3$): δ8.23 (dd, 1H), 8.03 (dd, 1H), 7.92 (ddd, 1H), 7.79 (ddd, 1H), 7.46 (m, 2H), 7.31 (m, 2H), 7.24 (m, 1H), 4.56 (s, 2H). ESI$^+$MS: calcd for C$_{18}$H$_{11}$N$_5$O: 313.32; found: 314.2 (MH$^+$).

3-Benzyl-1,2,3a,4,10-pentaaza-cyclopenta[b]fluoren-9-one (1k/B)

Prepared according to the general procedure B in 6% yield as yellow solid. $^1$H NMR (300 MHz, CDCl$_3$): δ 8.11 (dd, 1H), 8.04 (dd, 1H), 7.90 (ddd, 1H), 7.77 (ddd, 1H), 7.45 (m, 2H), 7.32 (m, 2H), 7.25 (m, 1H), 4.62 (s, 2H). ESI$^+$MS: calcd for C$_{18}$H$_{11}$N$_5$O: 313.32; found: 314.1 (MH$^+$).

General procedure C: synthesis of halo-pentaaza-cyclopenta[b]fluoren-9-one

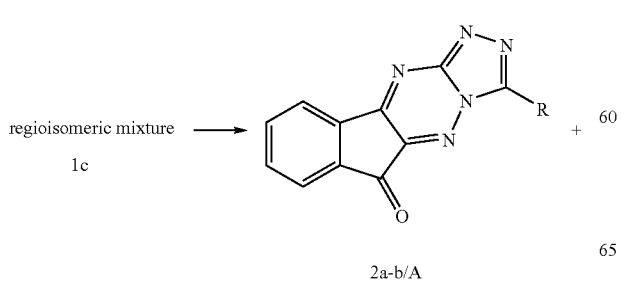

2a-b/A

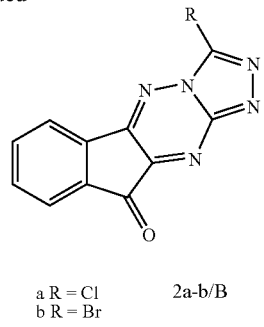

a R = Cl
b R = Br 2a-b/B

A regioisomeric mixture of amines 1c (400 mg, 1.68 mmol) was added in portions to a solution of tert-butyl nitrite (300 μl, 2.52 mmol) and copper(II) halide (2.52 mmol) in acetonitrile (8 ml) at 60° C. The mixture was heated at 80° C. for two hours, then it was cooled and the solvents evaporated. The crude was purified by flash chromatography (EtOAc/MeOH 99:1 or CH$_2$Cl$_2$/acetone 95:5).

1-Chloro-2,3,4,10,10a-pentaaza-cyclopenta[b]fluoren-9-one (2a/A)

Prepared according to the general procedure C in 49% yield as yellow solid as single regioisomer. $^1$H NMR (300 MHz, DMSO d$_6$): δ 8.29 (d, 1H), 8.07 (m, 2H), 7.95 (dd, 1H). ESI$^+$MS: calcd for C$_{11}$H$_4$ClN$_5$O: 257.64; found: 258.1 (MH$^+$).

1-Bromo-2,3,4,10,10a-pentaaza-cyclopenta[b]fluoren-9-one and 3-bromo-1,2,3a,4,10-pentaaza-cyclopenta[b]fluoren-9-one (2b)

Prepared according to the general procedure C in 69% yield as yellow solid as 6:4 regioisomeric mixture. $^1$H NMR (300 MHz, DMSO d$_6$) (mixture of isomers): δ 8.28 and 8323 (d, 1H), 8.10-7.86 (m, 3H). ESI$^+$MS: calcd for C$_{11}$H$_4$BrN$_5$O: 302.09; found: 302.0 (MH$^+$).

Synthesis of 6-(7)-chloro-methyl-pentaaza-cyclopenta[b]fluoren-9-one (3)

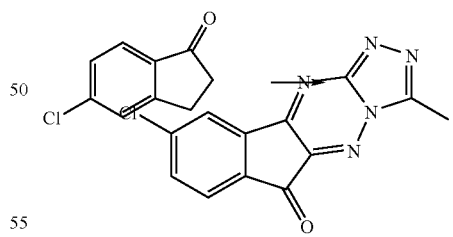

+

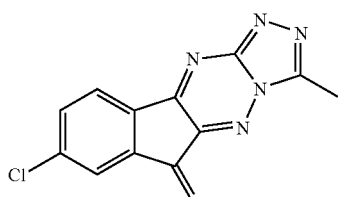

3/A

-continued

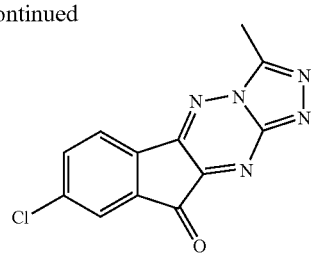

3/B

A solution of 5-chloro 1-indanone (0.97 g, 5.8 mmol) and N-bromo succinimide (2.1 g, 11.6 mmol) in DMSO (23 ml) was stirred 16 hours at 40° C. and 4 hours at 80° C. under vacuum. Brine (25 ml) was added and the mixture was extracted with $CH_2Cl_2$ (4×25 ml). The collected organic layers were dried over $Na_2SO_4$, filtered and evaporated. The crude was used without any further purification. For the condensation between the crude diaminotriazole and ninhydrin, see the General procedure A.

6-(7)-Chloro-1-methyl-2,3,4,10,10a-pentaaza-cyclopenta[b]fluoren-9-one (3/A)

Yield: 13%, yellow solid, 1:1 regioisomeric mixture: $^1$H NMR (300 MHz, $CDCl_3$) (mixture of isomers): δ 8.19 (d, 1H), 7.96 (d, 1H), 7.74 (dd, 1H), 2.84 (s, 3H). 8.17 (d, 1H), 7.97 (d, 1H), 7.86 (dd, 1H), 2.83 (s, 3H). ESI$^+$MS: calcd for $C_{12}H_6ClN_5O$: 271.67; found: 272.0 (MH$^+$).

7-Chloro-3-methyl-1,2,3a,4,10-pentaaza-cyclopenta[b]fluoren-9-one (3/B)

Yield: 3%, brownish solid: $^1$H NMR (300 MHz, $CDCl_3$): δ 8.03 (d, 1H), 7.90 (d, 1H), 7.65 (dd, 1H), 2.79 (s, 3H). ESI$^+$MS: calcd for $C_{12}H_6ClN_5O$: 271.67; found: 272.0 (MH$^+$).

General procedure D: synthesis of 2-alkyl-2H-1,2,3,4,10-pentaaza-cyclopenta[b]fluoren-9-one

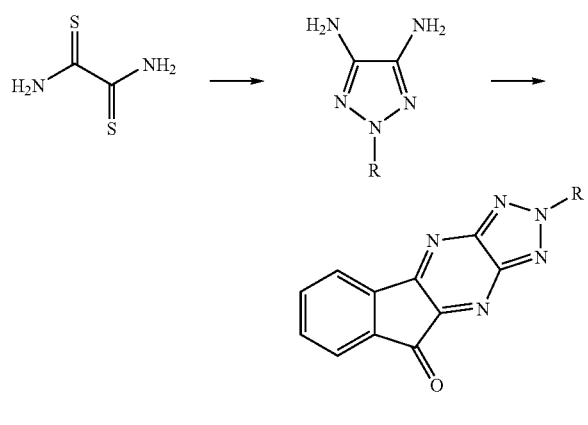

a R = Me
b R = Bn 4a-b/A

1-Methyl-3,4-diamino-1,2,5 triazole and 1-benzyl-3,4-diamino-1,2,5 triazole were prepared according to the procedure described in *Chem. Heterocycl. Compd.* 1992, 803, starting from dithiooxamide.

For the condensation between the crude diaminotriazole and ninhydrin, see the General procedure A. The raw product was purified by silica gel flash chromatography ($CH_2Cl_2$/MeOH 95:5).

2-Methyl-2H-1,2,3,4,10-pentaaza-cyclopenta[b]fluoren-9-one (4a)

Prepared according to the general procedure D in 12% yield as brown solid.
$^1$H NMR (300 MHz, DMSO $d_6$): δ 8.09 (d, 1H), 7.88 (m, 2H), 7.72 (ddd, 1H), 4.59 (s, 3H). ESI$^+$MS: calcd for $C_{12}H_7N_5O$: 237.22; found: 238.1 (MH$^+$).

2-Benzyl-2H-1,2,3,4,10-pentaaza-cyclopenta[b]fluoren-9-one (4b)

Prepared according to the general procedure D in 7% yield as brown solid.
$^1$H NMR (300 MHz, DMSO $d_6$): δ 8.07 (d, 1H), 7.88 (m, 2H), 7.73 (ddd, 1H), 7.51-7.33 (m, 5H), 6.05 (s, 2H). ESI$^+$MS: calcd for $C_{18}H_{11}N_5O$: 313.32; found: 314.1 (MH$^+$).

Representative Cysteine Proteases

USP5 Activity Assay

USP5 was diluted in USP buffer (50 mM Tris HCl; 0.5 mM EDTA; 5 mM DTT; 0.01% Triton X-100; Bovine Serum Albumin 0.05 mg.ml$^{-1}$ pH 7.6). Compounds stocks (100 mM) were stored at −20° C. in DMSO. Compounds were tested at the following final concentrations: 100 μM; 33.3 μM; 11.1 μM; 3.7 μM; 1.23 μM; 412 nM; 137 nM; 45.7 nM; 15.2 nM; 5 nM.

Reactions were performed as duplicates in Black LJL 96 well plates (HE microplates; Molecular Devices; 20 μl final reaction volume). The substrate concentration for USP5 was 400 nM Ub-AMC (Boston Biochem). The concentrations of the enzyme (USP5) in specificity assays was 300 pM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/− compounds) diluted in assay buffer. Reactions were incubated for 60 minutes at 37° C. Reactions were stopped by adding acetic acid (100 mM final). Readings were performed on a Pherastar Fluorescent Reader (BMG). λ Emission 380 nm; λ Excitation=460 nm. Data (mean values +/− standard deviation) were analyzed as % of control (no compound) and plotted as percentage versus the Log of the compound concentration using GraphPad (Prism). Data were fitted to a sigmoidal model (variable slope).

Cloning & Purification of USP7

The cDNA encoding USP7 was obtained by PCR amplification from placenta mRNA. USP7 cDNA was subcloned by PCR into a baculovirus expression vector (pFastBac-HT; Invitrogen). A cDNA encoding a mutated USP7 was generated by mutagenic PCR. The corresponding protein encodes a cysteine to alanine substitution at residue 223. The sequences were ascertained by sequencing of the entire open reading frame. Bacmids encoding USP7 were generated following DH10bac transposition. The corresponding bacmids were transfected into insect cells (Sf9). Viruses were recovered from culture supernatant and amplified twice. Insect cells (Sf9 or High Five; Invitrogen) were infected for 72 hours. Total cell lysates were harvested and lyzed in lysis buffer (Tris HCl 50 mM pH7.6; 0.75% NP40; 500 mM NaCl; 10% glycerol; 1 mM DTT; 10 mM imidazole; Protease Inhibitor. Cocktail; AEBSF 20 µg.ml$^{-1}$; Aprotinin 10 µg.ml$^{-1}$). Proteins were affinity purified on metal affinity resins (Talon Metal affinity resin; BD Biosciences). Bound materials were extensively washed in wash buffer (50 mM Sodium Phosphate pH7.0; 300 mM NaCl; 10 mM imidazole; 0.5% Triton X-100; 10% glycerol) and eluted from the resin in 250 mM imidazole-containing wash buffer. Proteins were dialyzed in dialysis buffer (Tris HCl pH 7.6 20 mM; NaCl 200 mM; DTT 1 mM; EDTA 1 mM; 10% Glycerol). Proteins purifications were analyzed on 4-12% NuPAGE (Invitrogen).

USP7 Activity Assay

USP7 was diluted in USP buffer (50 mM Tris HCl; 0.5 mM EDTA; 5 mM DTT; 0.01% Triton X-100; Bovine Serum Albumin 0.05 mg.ml$^{-1}$ pH7.6). Compounds stocks (100 mM) were stored at −20° C. in DMSO. Compounds were tested at the following final concentrations: 100 µM; 33.3 µM; 11.1 µM; 3.7 µM; 1.23 µM; 412 nM; 137 nM; 45.7 nM; 15.2 nM; 5 nM.

Reactions were performed as duplicates in Black LJL 96 well plates (HE microplates; Molecular Devices; 20 µl final reaction volume). The substrate concentration for USP7 was 400 nM Ub-AMC (*Chem. Biol.,* 2003, 10, p. 837-846) (Boston Biochem). The concentrations of the enzyme (USP7) in specificity assays was 152 pM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/−compounds) diluted in assay buffer. Reactions were incubated for 60 minutes at 37° C. Reactions were stopped by adding acetic acid (100 mM final). Readings were performed on a Pherastar Fluorescent Reader (BMG). λ Emission 380 nm; λ Excitation=460 nm. Data (mean values +/−standard deviation) were analyzed as % of control (no compound) and plotted as percentage versus the Log of the compound concentration using GraphPad (Prism). Data were fitted to a sigmoidal model (variable slope).

Cloning & Purification of USP8

The cDNA encoding USP8 was obtained by PCR amplification from placenta mRNA. USP8 cDNA was subcloned by PCR into a baculovirus expression vector (pFastBac-HT; Invitrogen). A cDNA encoding a mutated USP8 was generated by mutagenic PCR. The corresponding protein encodes a cysteine to alanine substitution at residue 786. The sequences were ascertained by sequencing of the entire open reading frame. Bacmids encoding USP7 were generated following DH10bac transposition. The corresponding bacmids were transfected into insect cells (Sf9). Viruses were recovered from culture supernatant and amplified twice. Insect cells (Sf9 or High Five; Invitrogen) were infected for 72 hours. Total cell lysates were harvested and lyzed in lysis buffer (Tris HCl 50 mM pH7.6; 0.75% NP40; 500 mM NaCl; 10% glycerol; 1 mM DTT; 10 mM imidazole; Protease Inhibitor Cocktail; AEBSF 20 µg.ml$^{-1}$; Aprotinin 10 µg.ml$^-$ 1). Proteins were affinity purified on metal affinity resins (Talon Metal affinity resin; BD Biosciences). Bound materials were extensively washed in wash buffer (50 mM Sodium Phosphate pH 7.0; 300 mM NaCl; 10 mM imidazole; 0.5% Triton X-100; 10% glycerol) and eluted from the resin in 250 mM imidazole-containing wash buffer. Proteins were dialyzed in dialysis buffer (Tris HCl pH 7.6 20 mM; NaCl 200 mM; DTT 1 mM; EDTA 1 mM; 10% Glycerol). Proteins purifications were analyzed on 4-12% NuPAGE (Invitrogen).

USP8 Activity Assay

USP8 was diluted in USP buffer (50 mM Tris HCl; 0.5 mM EDTA; 5 mM DTT; 0.01% Triton X-100; Bovine Serum Albumin 0.05 mg.ml$^{-1}$ pH8.8). Compounds stocks (100 mM) were stored at −20° C. in DMSO. Compounds were tested at the following final concentrations: 100 µM; 33.3 µM; 11.1 µM; 3.7 µM; 1.23 µM; 412 nM; 137 nM; 45.7 nM; 15.2 nM; 5 nM.

Reactions were performed as duplicates in Black LJL 96 well plates (HE microplates; Molecular Devices; 20 µl final reaction volume). The substrate concentration for USP8 was 400 nM Ub-AMC (Boston Biochem). The concentrations of the enzyme (USP8) in specificity assays was 630 pM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/−compounds) diluted in assay buffer. Reactions were incubated for 60 minutes at 37° C. Reactions were stopped by adding acetic acid (100 mM final). Readings were performed on a Pherastar Fluorescent Reader (BMG). λ Emission 380 nm; λ Excitation=460 nm. Data (mean values +/− standard deviation) were analyzed as % of control (no compound) and plotted as percentage versus the Log of the compound concentration using GraphPad (Prism). Data were fitted to a sigmoidal model (variable slope).

UCH-L3 Activity Assay

Uch-L3 was diluted in USP buffer (50 mM Tris HCl; 0.5 mM EDTA; 5 mM DTT; 0.01% Triton X-100; Bovine Serum Albumin 0.05 mg.ml$^{-1}$ pH7.6). Compounds stocks (100 mM) were stored at −20° C. in DMSO. Compounds were tested at the following final concentrations: 100 µM; 33.3 µM; 11.1 µM: 3.7 µM; 1.23 µM; 412 nM; 137 nM; 45.7 nM; 15.2 nM; 5 nM.

Reactions were performed as duplicates in Black LJL 96 well plates (HE microplates; Molecular Devices; 20 µl final reaction volume). The substrate concentration for Uch-L3 was 400 nM Ub-AMC (Boston Biochem). The concentration of the enzyme (Uch-L3) in specificity assays was 13 pM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/−compounds) diluted in assay buffer. Reactions were incubated for 60 minutes at 37° C. Reactions were stopped by adding acetic acid (100 mM final). Readings were performed on a Pherastar Fluorescent Reader (BMG). δ Emission 380 nm; δ Excitation=460 nm. Data (mean values +/− standard deviation) were analyzed as % of control (no compound) and plotted as percentage versus the Log of the compound concentration using GraphPad (Prism). Data were fitted to a sigmoidal model (variable slope).

Cloning & Purification of SENP1

The cDNA encoding SENP1 was obtained by PCR amplification from placenta mRNA. SENP1 cDNA was subcloned by PCR into a bacterial expression vector (pMAL-C2X; New England BioLabs, Inc). The sequence was ascertained by sequencing of the entire open reading frame. pMAL-C2-SENP1 was transformed into BL21 cells and grown in LB-ampicillin medium supplemented with glucose (2 g.l$^{-1}$). Fusion protein expression was induced by IPTG (0.5 mM). Bacterial cell lysates were harvested and lyzed in lysis buffer (Tris HCl 20 mM pH7.4; 1 mM EDTA; 200 mM NaCl; 0.5% Triton X-100; 10% glycerol; Protease Inhibitor Cocktail) followed by sonication. Proteins were affinity purified on amylose affinity resin (New England BioLabs, Inc). Bound materials were extensively washed in wash buffer (20 mM Tris HCl pH7.4; 200 mM NaCl; 1 mM EDTA; 0.5% Triton X-100; 10% glycerol) and eluted from the resin in 10 mM maltose-containing wash buffer. Proteins were dialyzed in dialysis buffer (Tris HCl pH 7.6 20 mM; NaCl 200 mM; DTT 1 mM; EDTA 1 mM; 10% Glycerol). Proteins purifications were analyzed on 4-12% NuPAGE (Invitrogen).

SENP1 Activity Assay

MBP-SENP1 was diluted in SENP1 buffer (50 mM Tris HCl; 0.5 mM EDTA; 5 mM DTT; 0.01% Triton X-100; Bovine Serum Albumin 0.05 mg.ml$^{-1}$ pH7.6). Compounds stocks (100 mM) were stored at −20° C. in DMSO. Compounds were tested at the following final concentrations: 100 µM; 33.3 µM; 11.1 µM; 3.7 µM; 1.23 µM; 412 nM; 137 nM; 45.7 nM; 15.2 nM; 5 nM.

Reactions were performed as duplicates in Black LJL 96 well plates (HE microplates; Molecular Devices; 20 µl final reaction volume). The substrate concentration for SENP1 was 200 nM SUMO-AMC (Chem. Biol., 2003, 10, p. 837-846) (Boston Biochem). The concentration of the enzyme (SENP1) in specificity assays was 1.8 nM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/− compounds) diluted in assay buffer. Reactions were incubated for 60 minutes at 37° C. Reactions were stopped by adding acetic acid (100 mM final). Readings were performed on a Pherastar Fluorescent Reader (BMG). λ Emission 380 nm; λ Excitation=460 nm. Data (mean values +/− standard deviation) were analyzed as % of control (no compound) and plotted as percentage versus the Log of the compound concentration using GraphPad (Prism). Data were fitted to a sigmoidal model (variable slope).

Caspase 3 Activity Assay

Caspase 3 was diluted in Caspase B buffer (100 mM Hepes pH 7.5; 10% sucrose; 0.1% CHAPS). Compounds stocks (100 mM) were stored at −20° C. in DMSO. Compounds were tested at the following final concentrations: 100 µM; 33.3 µM; 11.1 µM; 3.7 µM; 1.23 µM; 412 nM; 137 nM; 45.7 nM; 15.2 nM; 5 nM. Reactions were performed as duplicates in Black LJL 96 well plates (HE microplates; Molecular Devices; 20 µl final reaction volume). The substrate concentration for caspase 3 specificity assay was 500 nM (Ac-DEVD-AMC; Promega). The concentration of the enzyme (Caspase 3) in specificity assays was 3.2 nM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/− compounds) diluted in assay buffer. Reactions were incubated for 60 minutes at 37° C. Reactions were stopped by adding acetic acid (100 mM final) Readings were performed on a Pherastar Fluorescent Reader (BMG). δ Emission 380 nm; δ Excitation=460 nm. Data (mean values +/− standard deviation) were analyzed as % of control (no compound) and plotted as percentage versus the Log of the compound concentration using GraphPad (Prism). Data were fitted to a sigmoidal model (variable slope).

Cathepsin B Activity Assay

Cathepsin B was diluted in Cathepsin B buffer (20 mM Tris HCl pH 6.8; 1 mM EDTA; 1 mM DTT). Compounds stocks (100 mM) were stored at −20° C. in DMSO. Compounds were tested at the following final concentrations: 100 µM; 33.3 µM; 11.1 µM; 3.7 µM; 1.23 µM; 412 nM; 137 nM; 45.7 nM; 15.2 nM; 5 nM. Reactions were performed as duplicates in Black LJL 96 well plates (HE microplates; Molecular Devices; 20 µl final reaction volume). The substrate concentration for cathepsin B specificity assay was 36 µM (z-RR-AMC; Calbiochem). The concentration of the enzyme (Cathepsin B) in specificity assays was 3.6 nM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/− compounds) diluted in assay buffer. Reactions were incubated for 60 minutes at 37° C. Reactions were stopped by adding acetic acid (100 mM final). Readings were performed on a Pherastar Fluorescent Reader (BMG). δ Emission 380 nm; δ Excitation 460 nm. Data (mean values +/− standard deviation) were analyzed as % of control (no compound) and plotted as percentage versus the Log of the compound concentration using GraphPad (Prism). Data were fitted to a sigmoidal model (variable slope).

Cell Viability and Proliferation Methods

HCT116 Cell Viability and Proliferation Assay

HCT116 colon cancer cells were obtained from ATCC (American Type Culture Collection), and maintained in Mc Coy's 5A medium containing 10% FBS, 3 mM glutamine and 1% penicillin/streptomycin. Cells were incubated at 37° C. in a humidified atmosphere containing 5% $CO_2$.

Cell viability was assayed using the MTS technique in 96-well culture plates (CellTiter 96® Aqueous Non-Radioactive Cell Proliferation Assay, Promega) according to the manufacturer's instructions. MTS (3-(4,5-dimethylthiazol-2-yl)-5(3-carboxymethoxyphenyl)-2-(4-sulfophenyl)-2H-tetra-zolium) is a MTT-derived tetrazolium that is reduced in metabolically active cells into a soluble, cell-permeant formazan. The amount of formazan, detected by its absorbance at 492 nm is proportional to the number of living, metabolically active cells.

$10^3$ HCT116 cells were seeded per well. 24 hours later, the medium was changed and the cells treated in triplicate with the following concentrations of each compound: 10 µM-3.33 µM-1.11 µM-370 nM-123 nM-41 nM-14 nM and 5 nM. The compounds were diluted in 100% DMSO, whose final concentration on cells was kept at 0.5%.

Cells were incubated with the compounds for 72 hours, and their viability then assayed by the addition of MTS for 2 hours. Absorbance at 492 nm was measured directly from the 96-well culture plates. GI50 (Growth Inhibition 50) concentrations for each compound were calculated using a sigmoidal variable slope fit (Prism 4.0, Graphpad Softwares). Values represent mean of three independent experiments.

PC3 Cell Viability and Proliferation Assay

PC-3 prostate cancer cells were obtained from ATCC, and maintained in F-12K medium containing 7% FBS and 1% penicillin/streptomycin. Cells were incubated at 37° C. in a humidified atmosphere containing 5% $CO_2$.

Cell viability was assayed using the MTS technique in 96-well culture plates (CellTiter 96® Aqueous Non-Radioactive Cell Proliferation Assay, Promega) according to the manufacturer's instructions. MTS (3-(4,5-dimethyl-thiazol-2-yl)-5-(3-carboxymethoxyphenyl)-2-(4-sulfophenyl)-2H-tetrazolium) is a MTT-derived tetrazolium that is reduced in metabolically active cells into a soluble, cell-permeant formazan. The amount of formazan, detected by its absorbance at 492 nm is proportional to the number of living, metabolically active cells.

$2 \times 10^3$ PC3 cells were seeded per well. 24 hours later, the medium was changed and the cells treated in triplicate with the following concentrations of each compound: 10 µM-3.33 µM-1.11 µM-370 nM-123 nM-41 nM-14 nM and 5 nM. The compounds were diluted in 100% DMSO, whose final concentration on cells was kept at 0.5%.

Cells were incubated with the compounds for 72 hours, and their viability then assayed by the addition of MTS for 2 hours. Absorbance at 492 nm was measured directly from the 96-well culture plates. GI50 (Growth Inhibition 50) concentrations for each compound were calculated using a sigmoidal variable slope fit (Prism 4.0, Graphpad Softwares). Values represent mean of three independent experiments.

| RESULTS | |
|---|---|
| 1. Inhibition of cysteine protease activities | |
| USPs | |
| Experimental N° | USP 5 |
| Example 1b/A | 7.6 µM |
| Example 1b/B | 0.234 µM |
| Example 1c | 0.700 µM |
| Example 1c/A | 2.8 µM |
| Example 1c/B | 0.390 µM |
| Example 1d/A | 3.23 µM |
| Example 1d/B | 0.253 µM |
| Example 1e/A | >100 µM |
| Example 1e/B | 0.363 µM |
| Example 1f/A | 3.9 µM |
| Example 1f/B | 0.237 µM |
| Example 1g/A | >100 µM |
| Example 1g/B | 0.423 µM |
| Example 1h/A | 2.5 µM |
| Example 1h/B | 0.546 µM |
| Example 1i/A | >100 µM |
| Example 1i/B | 0.487 µM |
| Example 2a/A | 0.549 µM |
| Example 2b | |
| Example 3/A | 1.54 µM |
| Example 3/B | 0.260 µM |
| Example 4a | 23 µM |
| Example 4b | >100 µM |
| Experimental N° | USP 7 |
| Example 1b/A | 16.7 µM |
| Example 1b/B | 0.55 µM |
| Example 1c | 1.4 µM |
| Example 1c/A | 15.3 µM |
| Example 1c/B | 0.7 µM |
| Example 1d/A | 16.5 µM |
| Example 1d/B | 0.225 µM |
| Example 1e/A | >100 µM |
| Example 1e/B | 0.662 µM |
| Example 1f/A | 23 µM |
| Example 1f/B | 0.604 µM |
| Example 1g/A | >100 µM |
| Example 1g/B | 0.789 µM |
| Example 1h/A | 9.7 µM |
| Example 1h/B | 1.61 µM |
| Example 1i/A | >100 µM |
| Example 1i/B | 0.461 µM |
| Example 1j/A | — |
| Example 1j/B | 0.207 µM |
| Example 1k/A | 3.3 µM |
| Example 1k/B | 0.425 µM |
| Example 2a/A | 2.6 µM |
| Example 2b | |
| Example 3/A | 2.8 µM |
| Example 3/B | 0.522 µM |
| Example 4a | 51 µM |
| Example 4b | >100 µM |
| Experimental N° | USP 8 |
| Example 1b/A | 0.701 µM |
| Example 1b/B | 0.056 µM |
| Example 1c | 0.170 µM |
| Example 1c/A | 0.840 µM |
| Example 1c/B | 0.081 µM |
| Example 1d/A | 0.537 µM |
| Example 1d/B | 0.055 µM |
| Example 1e/A | 0.952 µM |
| Example 1e/B | 0.169 µM |
| Example 1f/A | 0.830 µM |
| Example 1f/B | 0.151 µM |
| Example 1g/A | 0.538 µM |
| Example 1g/B | 0.167 µM |
| Example 1h/A | 0.67 µM |
| Example 1h/B | 0.164 µM |
| Example 1i/A | 0.256 µM |
| Example 1i/B | 0.188 µM |
| Example 1j/A | 2.5 µM |
| Example 1j/B | 0.046 µM |
| Example 1k/A | 0.663 µM |
| Example 1k/B | 0.166 µM |
| Example 2a/A | 0.128 µM |
| Example 2b | |
| Example 3/B | 0.119 µM |
| Example 3/A | 0.301 µM |
| Example 4a | 10 µM |
| Example 4b | 15 µM |
| UCH-L3 | |
| Experimental N° | Uch-L3 |
| Example 1b/A | 0.516 µM |
| Example 1b/B | 0.143 µM |
| Example 1c | 0.240 µM |
| Example 1c/A | 0.860 µM |
| Example 1c/B | 0.133 µM |
| Example 1d/A | 0.430 µM |
| Example 1d/B | 0.095 µM |
| Example 1e/A | 1.27 µM |
| Example 1e/B | 0.168 µM |
| Example 1f/A | 0.364 µM |
| Example 1f/B | 0.091 µM |
| Example 1g/A | 0.636 µM |
| Example 1g/B | 0.183 µM |
| Example 1h/A | 0.39 µM |
| Example 1h/B | 0.158 µM |
| Example 1j/A | 1.9 µM |

-continued

RESULTS

| | |
|---|---|
| Example 1j/B | 0.055 μM |
| Example 1k/A | 0.598 μM |
| Example 1k/B | 0.164 μM |
| Example 1i/A | 0.261 μM |
| Example 1i/B | 0.202 μM |
| Example 2a/A | 0.133 μM |
| Example 2b | — |
| Example 3/BA | 0.071 323 μM |
| Example 3/AB | 0.323 071 μM |
| Example 4a | 3.4 μM |
| Example 4b | 7.8 μM |

SENP1

| Experimental N° | SENP1 |
|---|---|
| Example 1b/A | >100 μM |
| Example 1b/B | 0.706 μM |
| Example 1c/A | |
| Example 1c/B | 0.731 μM |
| Example 1d/A | >100 μM |
| Example 1d/B | 0.415 μM |
| Example 1e/A | 5.88 μM |
| Example 1e/B | 0.694 μM |
| Example 1f/A | >100 μM |
| Example 1f/B | 0.229 μM |
| Example 1g/A | >100 μM |
| Example 1g/B | 0.954 μM |
| Example 1h/A | >100 μM |
| Example 1h/B | 1.02 μM |
| Example 1j/A | >100 μM |
| Example 1j/B | 0.299 μM |
| Example 1k/A | >100 μM |
| Example 1k/B | 1.21 μM |
| Example 1i/A | 22.1 μM |
| Example 1i/B | 1.09 μM |
| Example 2a/A | |
| Example 2b | |
| Example 3/A | >100 μM |
| Example 3/B | 0.855 μM |

Caspase 3

| Experimental N° | Caspase 3 |
|---|---|
| Example 1b/A | 4.1 μM |
| Example 1b/B | 0.424 μM |
| Example 1c | |
| Example 1c/A | 3.7 μM |
| Example 1d/B | 0.212 μM |
| Example 1d/A | 11.6 μM |
| Example 1d/B | 0.467 μM |
| Example 1e/A | >100 μM |
| Example 1e/B | 0.727 μM |
| Example 1f/A | 4.6 μM |
| Example 1f/B | 0.475 μM |
| Example 1g/A | >100 μM |
| Example 1g/B | 0.629 μM |
| Example 1h/A | 3.9 μM |
| Example 1h/B | 1.02 μM |
| Example 1i/A | 0.926 μM |
| Example 1i/B | 0.556 μM |
| Example 1j/A | 1.9 μM |
| Example 1j/B | 0.188 μM |
| Example 1k/A | 0.598 μM |
| Example 1k/B | 0.164 μM |
| Example 3/A | 1.51 μM |
| Example 3/B | 0.743 μM |

Cathepsine B

| Experimental N° | Cathepsin B |
|---|---|
| Example 1b/A | 24 μM |
| Example 1b/B | 0.182 μM |
| Example 1c | |
| Example 1c/A | 5.0 μM |

-continued

RESULTS

| | |
|---|---|
| Example 1c/B | 0.103 μM |
| Example 1d/A | |
| Example 1d/B | 0.150 μM |
| Example 1e/A | 5.41 μM |
| Example 1e/B | 0.267 μM |
| Example 1f/A | 6.5 μM |
| Example 1f/B | 0.233 μM |
| Example 1g/A | 4.62 μM |
| Example 1g/B | 0.264 μM |
| Example 1h/A | 30 μM |
| Example 1h/B | 0.547 μM |
| Example 1i/A | 1.02 μM |
| Example 1i/B | 0.314 μM |
| Example 1j/B | 0.181 μM |
| Example 1k/B | 0.363 μM |
| Example 2a/A | 12 μM |
| Example 2b | |
| Example 3/A | 17.4 μM |
| Example 3/B | 0.147 μM |
| Example 4a | >100 μM |
| Example 4b | |

2. Inhibition of cell viability and proliferation

| Experimental N° | HCT116 GI50 D3 |
|---|---|
| Example 1b/A | 1.3 μM |
| Example 1b/B | 0.084 μM |
| Example 1c | 1.5 μM |
| Example 1c/A | 8.5 μM |
| Example 1c/B | 0.981 μM |
| Example 1d/A | 1.4 μM |
| Example 1d/B | 0.059 μM |
| Example 1e/A | 3.1 μM |
| Example 1e/B | 0.067 μM |
| Example 1f/A | 1.357 μM |
| Example 1f/B | 0.040 μM |
| Example 1g/A | 3.0 μM |
| Example 1g/B | 0.053 μM |
| Example 1h/A | 2.05 μM |
| Example 1h/B | 0.323 μM |
| Example 1i/A | 1.285 μM |
| Example 1i/B | 0.065 μM |
| Example 2a/A | 0.581 μM |
| Example 2b | |
| Example 3/B | 0.098 μM |
| Example 3A | 0.361 μM |
| Example 4a | >10 μM |
| Example 4b | >10 μM |

PC3

| Experimental N° | PC3 GI50 D3 |
|---|---|
| Example 1b/A | 7.09 μM |
| Example 1b/B | 0.334 μM |
| Example 1c | 4.0 μM |
| Example 1c/A | >10 μM |
| Example 1c/B | 3.17 μM |
| Example 1d/A | 5.4 μM |
| Example 1d/B | 0.256 μM |
| Example 1e/A | 4.2 μM |
| Example 1e/B | 0.175 μM |
| Example 1f/A | 3.8 μM |
| Example 1f/B | 0.096 μM |
| Example 1g/A | 4.0 μM |
| Example 1g/B | 0.162 μM |
| Example 1h/A | 4.0 μM |
| Example 1h/B | 1.442 μM |
| Example 1i/A | 1.751 μM |
| Example 1i/B | 0.238 μM |
| Example 2a/A | 0.983 μM |
| Example 2b | |
| Example 3/B | 0.286 μM |
| Example 3A | 0.994 μM |

-continued

| RESULTS | |
|---|---|
| Example 4a | >10 μM |
| Example 4b | >10 μM |

The invention claimed is:

1. A compound of formula (Ib):

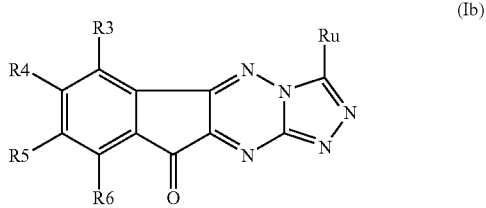

wherein,

Ru is selected from the group consisting of CN, =O, Hal, Alk, OAlk, OH, NRCN, C(CN)=C(OH)(OAlk), SR, NRR', C(O)NRR', Heterocycle, Aryl, Heteroaryl, and Cycloalkyl, wherein Alk, Aryl, Heteroaryl, Heterocycle, and Cycloalkyl are optionally substituted by Hal, NRR', CN, OH, $CF_3$, Aryl, Heteroaryl, or OAlk;

R3, R4, R5, R6 are each identical or different and are independently chosen from the group consisting of H, OAlk, Alk, Hal, NRR', CN, OH, OCF3, CF3, Aryl, and Heteroaryl;

R and R' are each identical or different and are independently selected from the group consisting of H and Alk, wherein Alk is optionally substituted by Hal, NRR', CN, OH, $CF_3$, Aryl, or Heteroaryl;

or, their pharmaceutically acceptable salts, or their optical isomers, racemates, diastereomers or enantiomers.

2. The compound according to claim 1, wherein Ru is selected from the group consisting of Aryl, Alk, NRR', Hal, -AlkAryl, -AlkOH, -AlkOAlk, and -Cycloalkyl.

3. The compound according to claim 1, wherein R3, R4, R5, R6 are each identical or different and are independently selected from the group consisting of H, Hal, Alk, OAlk, and $OCF_3$.

4. The compound according to claim 1, wherein the compound is selected from the group consisting of:

3-Methyl-1,2,3a,4,10-pentaaza-cyclopenta[b]fluoren-9-one

3-Amino-1,2,3a,4,10-pentaaza-cyclopenta[b]fluoren-9-one

3-Ethyl-1,2,3a,4,10-pentaaza-cyclopenta[b]fluoren-9-one

3-Propyl-1,2,3a,4,10-pentaaza-cyclopenta[b]fluoren-9-one

3-Butyl-1,2,3a,4,10-pentaaza-cyclopenta[b]fluoren-9-one

3-Isobutyl-1,2,3a,4,10-pentaaza-cyclopenta[b]fluoren-9-one

3-Hydroxymethyl-1,2,3a,4,10-pentaaza-cyclopenta[b]fluoren-9-one

3-Methoxymethyl-1,2,3a,4,10-pentaaza-cyclopenta[b]fluoren-9-one

3-Cyclopropyl-1,2,3a,4,10-pentaaza-cyclopenta[b]fluoren-9-one

3-Benzyl-1,2,3a,4,10-pentaaza-cyclopenta[b]fluoren-9-one 3-bromo-1,2,3a,4,10-pentaaza-cyclopenta[b]fluoren-9-one 7-Chloro-3-methyl-1,2,3a,4,10-pentaaza-cyclopenta[b]fluoren-9-one or their pharmaceutically acceptable salts, or their optical isomers, racemates, diastereomers or enantiomers.

5. Process for the preparation of the compound according to claim 1 comprising the step of reacting a corresponding compound of formula (Ib'):

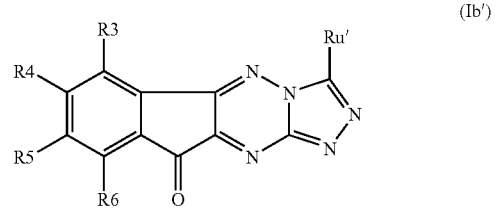

wherein R3, R4, R5, R6, and Ru are defined as in claim 1, and wherein Ru' is a precursor group of a corresponding Ru by one or more steps allowing the precursor group to be transformed into the desired Ru group, and optionally isolating the compound of formula (Ib).

6. Process for the preparation of the compound according to claim 1 comprising the step of reacting corresponding compounds of formula (IIb) and (IIIb):

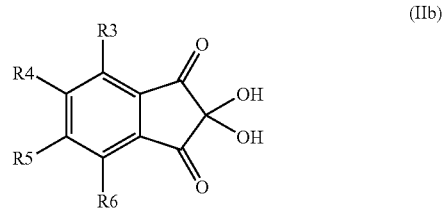

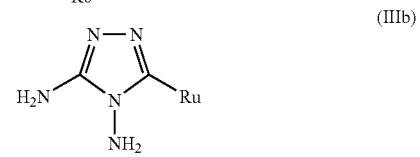

wherein R3, R4, R5, R6, and Ru are defined as in claim 1.

7. The process according to claim 6, wherein the reaction is carried out in an organic protic solvent in the presence of an acid.

8. A pharmaceutical composition comprising the compound according to claim 1, and a pharmaceutically acceptable carrier.

9. The pharmaceutical composition according to claim 8, wherein the compound is selected from the group consisting of:

3-Methyl-1,2,3a,4,10-pentaaza-cyclopenta[b]fluoren-9-one

3-Amino-1,2,3a,4,10-pentaaza-cyclopenta[b]fluoren-9-one

3-Ethyl-1,2,3a,4,10-pentaaza-cyclopenta[b]fluoren-9-one

3-Propyl-1,2,3a,4,10-pentaaza-cyclopenta[b]fluoren-9-one

3-Butyl-1,2,3a,4,10-pentaaza-cyclopenta[b]fluoren-9-one

3-Isobutyl-1,2,3a,4,10-pentaaza-cyclopenta[b]fluoren-9-one

3-Hydroxymethyl-1,2,3a,4,10-pentaaza-cyclopenta[b]fluoren-9-one
3-Methoxymethyl-1,2,3a,4,10-pentaaza-cyclopenta[b]fluoren-9-one
3-Cyclopropyl-1,2,3a,4,10-pentaaza-cyclopenta[b]fluoren-9-one
3-Benzyl-1,2,3a,4,10-pentaaza-cyclopenta[b]fluoren-9-one
3-bromo-1,2,3a,4,10-pentaaza-cyclopenta[b]fluoren-9-one
7-Chloro-3-methyl-1,2,3a,4,10-pentaaza-cyclopenta[b]fluoren-9-one or their pharmaceutically acceptable salts, or their optical isomers, racemates, diastereomers or enantiomers.

* * * * *